United States Patent [19]

Connor et al.

[11] Patent Number: 4,910,317

[45] Date of Patent: Mar. 20, 1990

[54] BENZOFURANS AND BENZOTHIOPHENES HAVING ANTIALLERGIC ACTIVITY AND METHOD OF USE THEREOF

[75] Inventors: David T. Connor, Ann Arbor; Michael D. Mullican, Ypsilanti; Roderick J. Sorenson; David O. Thueson, both of Ann Arbor, all of Mich.

[73] Assignee: Warner-Lambert Company, Morris Plains, N.J.

[21] Appl. No.: 210,206

[22] Filed: Jun. 27, 1988

Related U.S. Application Data

[63] Continuation-in-part of Ser. No. 191,699, May 17, 1988, which is a continuation-in-part of Ser. No. 73,554, Jul. 14, 1987, abandoned.

[51] Int. Cl.$^4$ .................... C07D 257/04; A61K 31/41
[52] U.S. Cl. ..................................... 514/381; 548/251
[58] Field of Search ......................... 548/251; 514/381

[56] References Cited

U.S. PATENT DOCUMENTS 4,140,785 2/1979 Hoffman et al. ................ 424/273 P
4,663,347 3/1987 Atkinson et al. ................... 548/251

FOREIGN PATENT DOCUMENTS 0028063 5/1981 European Pat. Off. .
0146243 6/1985 European Pat. Off. .
0187487 7/1986 European Pat. Off. .

Primary Examiner—David B. Springer
Attorney, Agent, or Firm—Joan Thierstein

[57] ABSTRACT

Novel benzothiophenes having antiallergic activity and both novel and other selected benzothiophenes having activity for treating acute respiratory distress syndrome. The benzothiophenes of the present invention are particularly 2-tetrazolylcarboxamides of the benzothiophenes.

16 Claims, No Drawings

BENZOFURANS AND BENZOTHIOPHENES HAVING ANTIALLERGIC ACTIVITY AND METHOD OF USE THEREOF

This is a continuation-in-part of U.S. patent application No. 191,699, filed May 17, 1988, which is a continuation-in-part of U.S. application Ser. No. 73,554, filed July 14, 1987, abandoned.

BACKGROUND OF THE INVENTION

Benzothiophene and benzofuran compounds are known as, for example, disclosed in European Patent Application No. 0146243 and copending U.S. patent application Ser. No. 790,664 now U.S. Pat. No. 4,703,053. Additionally, European Patent Application No. 69,521 and U.S. Pat. No. 3,452,039 disclose various benzothiophene derivatives.

However, additional novel benzothiohene and benzofuran derivatives having selected substituents which substituents are not made obvious by the above noted references are now found to prevent the release of mediators including histamine and leukotrienes from basophils and mast cells, and prevent respiratory burst in neutrophils providing activity useful in treatment of cardiovascular disorders as well as an antiinflammatory, antipsoriatic, antiulcer, antimigraine and particularly as an antiallergy agent. That is, the novel agents of the present invention act as inhibitors of cell activation for the above noted diseases and in the same manner as described in U.S. patent application No. 790,664 now U.S. Pat. No. 4,703,053 which is hereby incorporated by reference.

Thus, the present invention is for novel compounds, that are benzothiophene and benzofuran derivatives, compositions and methods of use therefor, as well as methods of preparation thereof.

Further, although U.S. patent application Ser. No. 790,664 now U.S. Pat. No. 4,703,053 discloses compounds having the activity of preventing respiratory burst in neutrophils the present invention is further for a method of using selected benzothiophenes and benzofurans particularly for treating acute respiratory distress syndrome (ARDS) in mammals, particularly humans, in need thereof comprising administering an anti-ARDS effective amount of the selected benzothiophenes an benzofurans in unit dosage form.

SUMMARY OF THE INVENTION

The present invention is a compound of the formula (I)

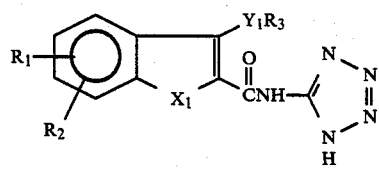

and pharmaceutically acceptable salts thereof; wherein
(1) $X_1$ and $Y_1$ are independently oxygen or sulfur;
(2) $R_1$ and $R_2$ are independently hydrogen or $OR_4$ wherein $R_4$ is hydrogen, lower alkyl, aryl, or aralkyl with the proviso that $R_1$ and $R_2$ cannot both be hydrogen at once; and
(3) $R_3$ is lower alkyl, aryl, or aralkyl with the proviso that $R_1$ and $R_2$ cannot both be hydrogen at once; with the proviso that when $R_1$ and $R_2$ are independently hydroxy or alkoxy then $R_3$ cannot be lower alkyl or aralkyl.

The present invention is, thus, also a pharmaceutical composition for treating diseases or conditions, such as acute respiratory distress syndrome, allergy, cardiovascular disorders, ulcers, inflammation, psoriasis, ischemic disorders (stroke, TIA, hernia, embolism and thrombus), and migraine which comprises an effective amount for treating each of the diseases or the conditions of the compound of the Formula I and a pharmaceutically acceptable carrier.

Also the present invention is a method of treating allergy, cardiovascular disorders, inflammation, psoriasis, or migraine in a mammal, particularly human, suffering therefrom which comprises administering the compound of Formula I in unit dosage form.

Finally, the present invention is a method of treating ARDS in a mammal, particularly human, suffering therefrom which comprises administering a compound of the formula (II)

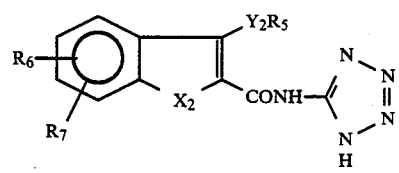

and pharmaceutically acceptable salts thereof; wherein
(1) $X_2$ and $Y_2$ are independently oxygen or sulfur;
(2) $R_6$ and $R_7$ are independently hydrogen, halogen or $OR_8$ wherein $R_8$ is hydrogen, lower alkyl, aryl, or aralkyl with the proviso that $R_6$ and $R_7$ cannot both be hydrogen at the same time; and
(3) $R_5$ is hydrogen, lower alkyl, aryl or aralkyl; in a unit dosage form.

Additionally, the present invention is also a novel process for making the compounds of the Formula I above, comprising Step (1) contacting a compound of the formula III

wherein $R_3$ and $Y_1$ are as defined above and NaH; with a compound of the formula (IV)

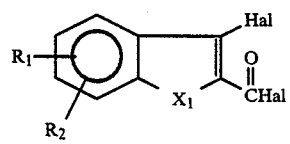

wherein $X_1$, $R_1$ and $R_2$ are as defined above and Hal is chloro or bromo; to obtain the compound of the formula (IVa)

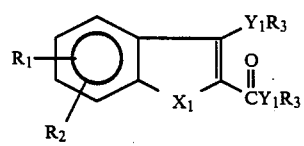

Step (2) treating a compound of the Formula IVa with aqueous base, preferably 1N NaOH, in methanol and tetrahydrofuran to obtain the compound of the formula (V)

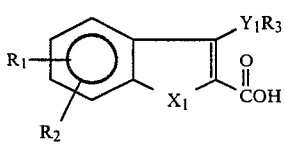

wherein $X_1$, $Y_1$, $R_1$, $R_2$, and $R_3$ are as defined above and

Step (3) contacting the compound of Formula V with a compound of the formula (VI) in the presence of a condensing agent

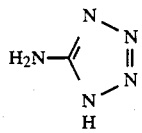

to obtain the compound of the Formula I.

The Step 1 is a novel process and, therefore, is itself also the present invention. However, Steps 1 and 2 may be a one pot reaction.

DETAILED DESCRIPTION OF THE INVENTION

Lower alkyl is of from one to six carbons, including methyl, ethyl, propyl, butyl, pentyl, hexyl or isomers thereof.

Aryl is phenyl or substituted phenyl having one or two substituents, such as halogen, trifluoromethyl, lower alkyl, lower alkoxy, hydroxy, lower alkylthio, $COOR_{10}$ wherein $R_{10}$ is hydrogen or lower alkyl, nitro, amino, substituted amino, and the like.

Lower alkoxy is of from one to six carbons, including methoxy, ethoxy, propoxy, butoxy, pentoxy, hexoxy or isomers thereof.

Substituted amino is mono- or di-loweralkylamino.

Halogen is chloro, bromo, fluoro, or iodo.

Aralkyl is aryl attached to the benzothiophene or benzofuran ring system through a lower alkylenyl carbon chain, straight or branched of from one to four carbons.

Generally, the novel process of the present invention for the preparation of the compounds of the Formula I are shown in the following Schemes A, B, and C.

Scheme A (Step 1)

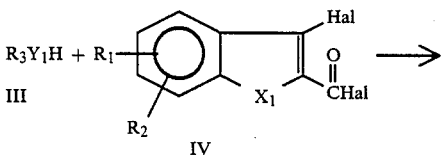

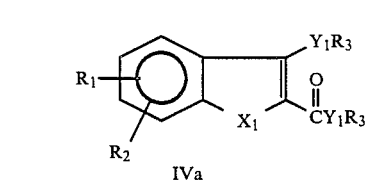

Scheme B (Step 2)

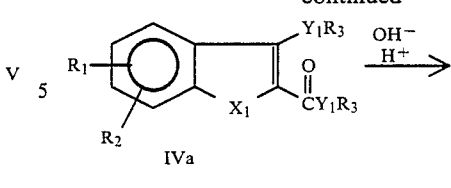

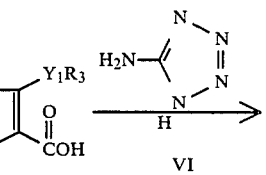

Scheme C (Step 3)

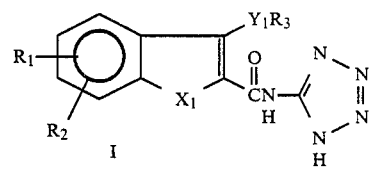

In each of compounds I, III, IV, IVa, and V the substituents $X_1$, $Y_1$, $R_1$, $R_2$, and $R_3$ are as defined above.

The compounds of the Formula IV are prepared in a manner analogous to that described by Sudabeh Pakray and Raymond N. Castle in *J. Heterocyclic Chem.*, 1986, 23, p. 1571. The remaining starting materials, i.e., the compounds of the Formula III and of the Formula VI are commercially available, are known, or can be prepared by known methods.

A hot solution; of about 50° C. to 130° C., of the compound of the Formula IV as defined above in a solvent such as tetrahydrofuran (THF), ether, o-dichlorobenzene and mixtures thereof or the like, preferably THF, is added rapidly to a 0° C.–25° C. solution of $R_3Y_1Na$ in THF (generated from the addition of a solution $R_3X_1H$ in THF to a slurry of NaH, preferably 60% in oil dispersion in THF at about 0° C. to room temperature) or o-dichlorobenzene. The resulting mixture is stirred at about 0° C. to room temperature for at least fifteen minutes then refluxed for from 0.5 hours to 100 hours, preferably for about three to twenty-two hours. Also, addition of tris[2-(2-methoxyethoxy) ethyl-]amine, that is described in U.S. Pat. No. 4,287,125, to the mixture after refluxing for 0.5 to 3 hours, although optional, is preferred. The resulting product of the Formula IVa may be isolated by conventional means such as extraction, distillation, chromatography, and the like, or may be used by further treating in crude form.

The further steps 2 and 3 above as shown in Schemes B and C are analogous to the saponification and conversion as described for the compounds of the U.S. patent Application Ser. No. 790,664 now U.S. Pat. No. 4,703,053 noted above whereby 5-aminotetrazole is reacted with the carboxylic acid moiety of the present compound of the Formula V.

Variations within that known to one of skill in the art is included in the descriptions of either Step 1 or 2 as described above or as described in the U.S. patent application Ser. No. 790,664, now U.S. Pat. No. 4,703,053.

The pharmaceutically acceptable salts of the compounds of the Formula I of the present invention are also as described for the compounds in the U.S. patent application Ser. No. 790,664 now U.S. Pat. No. 4,703,053 or are as understood by the ordinarily skilled artisan. For example, see "Pharmaceutical Salts," by Berge, S. M. et al, in *The Journal of Pharmaceutical Sciences*, Vol. 66, No. 1, January, 1977, pp. 1–19.

The antiallergy activity of the compounds having the Formula I of the present invention is determined by the well-known Schultz-Dale procedure that is described in N. Chand, et al, *Agents and Actions*, 8, 171 (1978) or the Herxheimer in vivo antiallergy test described in H. Herxheimer, *J. Physiol.* (London), Vol. 117, 251 (1952).

By virtue of this antiallergy activity the compounds of Formula I are useful in treating an allergic hypersensitivity reaction (AHR) having broad symptoms. For example, the symptoms may include pruritus, erythema, edema, dermatitis, lacrimation, nasal discharge, coughing, sneezing, nausea, vomiting, diarrhea, difficulty in breathing, pain, inflammation, and in severe cases, anaphylactic shock, circulatory collapse, and even death. The AHR is found in man as well as other animals suffering from bronchial asthma, seasonal pollinosis (e.g., hay fever), allergic rhinitis, contact allergies (poison oak and ivy, etc), urticaria, allergic conjunctivitis, food allergies, and anaphylactoid reactions.

In an AHR an antigen or cytokine influences the cell membrane of a mast cell by reacting with an antibody or receptor, to initiate reactions within the mast cell which ultimately causes the production and release of mediators (bioactive compounds) such as bradykinin, slow reacting substance of anaphylaxis (SRS-A), histamine, serotonin (5HT), thromboxanes, prostaglandins, or other not now known substances. The mediator(s) is released from the mast cell whereupon t attaches to suitable receptor sites (e.g., on smooth muscle) resulting in AHR attack symptoms. Various methods are used to relieve the symptoms of AHR. It is not known, however, what mechanism is effected for the antiallergic use by the compounds having Formula I of the present invention.

Pharmaceutical compositions are prepared from compounds of Formula I and salts thereof having inert pharmaceutical carriers. The composition may be either solid or liquid.

A physician or veterinarian of ordinary skill readily determines a subject who is exhibiting AHR symptoms. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, pills, liquids, syrups, powders, or granules. They also may be administered rectally or vaginally in such forms as suppositories or bougies; they may also be introduced parenterally (e.g., subcutaneously, intravenously, or intramuscularly, using forms known to the pharmaceutical art. They are also introduced directly to an affected area (e.g., in the form of eye drops or by inhalation). For the treatment of AHR induced conditions such as erythema, the compounds of the present invention may also be administered topically in the form of ointments, creams, gels, or the like. In general, the preferred route of administration is orally; except for emergency treatment where the parenteral route is preferred.

An effective but nontoxic quantity of the compound is employed in treatment. The ordinarily skilled physician or veterinarian will readily determine and prescribe the effective amount of the anti-AHR agent to prevent or arrest the progress of the condition. In so proceeding, the physician or veterinarian could employ relatively low dosages at first, subsequently increasing the dose until a maximum response is obtained.

Initial dosages of the compounds of the invention having Formula I or II are ordinarily in the area of 10 mg up to 2 g per day orally, preferably 10 mg to 500 mg per dose orally, given from one to four times daily or as needed. When other forms of administration are employed equivalent doses are administered.

Preferably, the pharmaceutical preparation from compounds of Formula I or II is in unit dosage form. The quantity of active compound in a unit dose of preparation may be varied or adjusted from 1 mg to 500 mg, preferably to 1 to 200 mg according to the particular application and the potency of the active ingredient. The compositions can, if desired, also contain other compatible therapeutic agents.

The compounds of Formula II are found to be particularly useful for the treatment of ARDS as shown by an assay demonstrating the inhibition of oxygen radical production by human neutrophils for representative compounds of the Formula II by two assays. The one assay provides $IC_{50}$'s for the inhibition of superoxide generation. DeChatelet, L. R., Shirley, P. S. and Johnson, R. B. 1976. Effect of phorbol myristate acetate on the oxidative metabolism of human polymorphonuclear leukocytes. Blood 47:545–554. The other assay is a generally recognized in vivo assay to show activity useful for treating ARDS. The in vivo assay is described in J. Clin. Invest., Vol. 69, May 1982, pp 1126–1135.

The representative compounds tested in the in vitro assay for the inhibition of superoxide generation are:
1. 5-Methoxy-3-(1-methylethoxy)-N-1H-tetrazol-5-yl-benzo[b]thiophene-2-carboxamide.
2. 6-Methoxy-3-(1-methylethoxy)-N-1H-tetrazol-5-yl-benzo[b]thiophene-2-carboxamide.
3. 5-Methoxy-3-[(1-methylethyl)thio-N-1H-tetrazol-5-yl]-benzo[b]thiophene-2-carboxamide.
4. 6-Methoxy-3-(1-methylethoxy)-N-1H-tetrazol-5-yl-2-benzofurancarboxamide.
5. 3-Benzyloxy-5-methoxy-N-1H-tetrazol-5-yl-benzo[b]thiophene-2-carboxamide.
6. 5-Methoxy-3-phenoxy-N-1H-tetrazol-5-yl-benzo[b]thiophene-2-carboxamide.

The activity for each of these compounds as numbered above is expressed as $IC_{50}$'s for the inhibition of superoxide generation and is shown in the following Table A:

TABLE A

| Above Compound No. | $R_6$ | $R_5$ | X | Y | $IC_{50}$ ($\mu$M) Inhibition of $O_2$-generation from neutrophils |
|---|---|---|---|---|---|
| 1 | 5-methoxy | 1-methylethyl | S | O | 19 |
| 2 | 6-methoxy | 1-methylethyl | S | O | 37 |
| 3 | 5-methoxy | 1-methylethyl | S | S | 23 |
| 4 | 6-methoxy | 1-methylethyl | O | O | 75 |
| 5 | 5-methoxy | benzyl | S | O | 23 |

TABLE A-continued

| Above Compound No. | R₆ | R₅ | X | Y | IC$_{50}$ (μM) Inhibition of O$_2$-generation from neutrophils |
|---|---|---|---|---|---|
| 6 | 5-methoxy | phenyl | S | O | 10 |

Further, activity for compounds of examples noted in the following Table A₁ likewise show IC$_{50}$'s for the inhibition of superoxide generation.

TABLE A1

| Example No. | R₅ | R₆ | IC$_{50}$ (μM) Inhibition of O$_2$-generation from neutrophils |
|---|---|---|---|
| C21C | Ph | 5,6-diOMe | 6 |
| C21D | Ph | 6-OMe | >100 |
| C21A | CH₂Ph | 5,6-diOMe | 40 |
| C20A | CHMe₂ | 5-OH | 48 |

Accordingly, the compounds of tee Formula II are now found to be particularly useful for treating ARDS shown by the inhibition of cobra venom factor (CVF) induced lung injury in rats using the Compound No. I above in the in vivo assay shown as follows in Table B:

TABLE B
Inhibition of CVF Induced Lung Injury in Rats by Compound No. 1 Above

| Treatment | Number of Animals | Lung Injury (x ± SEM) | Protection % Inhibition of Injury |
|---|---|---|---|
| Exp. A. | | | |
| Saline (control) | 5 | 0.20 ± 0.01 | |
| CVF Treatment | 7 | 1.45 ± 0.19 | |
| CVF + Compound No. 1, i.v.* | 5 | 0.48 ± 0.08 | 76 |
| CVF + Compound No. 1, i.p.** | 4 | 0.73 ± 0.06 | 58 |

*Compound No. 1 above was given intravenously (20 mg/kg) 10 minutes before intravenous injection of CVF (20 mg/kg).
**Compound No. 1 above was injected intraperitoneally (20 mg/kg) 20 minutes before CVF.

The following examples elaborate the compounds of the Formula I of the present invention but are not meant to be limiting thereto.

EXAMPLES

EXAMPLE 1

3-Benzyloxy-5-methoxy-N-1H-tetrazol-5-yl-benzo[b]-thiophene-2-carboxamide.

Step 1. A solution of 13.1 g (120.8 mmol, 2.8 equiv) of benzyl alcohol in 35 ml of dry tetrahydrofuran is added dropwise over 10 minutes to a room temperature slurry of 4.3 g (107.5 mmol, 2.5 equiv) of 60% NaH oil dispersion in 65 ml of tetrahydrofuran under nitrogen atmosphere. The reaction is stirred for 15 minutes then cooled in an ice-water bath. A hot solution of 11.4 g (43.7 mmol) 3-chloro-5-methoxybenzo[b]thiophene-2-carbonylchloride (prepared by the method described by Sudabeh Pakray and Raymond N. Castle in *J. Heterocyclic Chem.*, 1986, 23, 1571) in 95 ml of tetrahydrofuran is added rapidly to the 0° C. reaction mixture. The reaction is stirred at 0° C. for 15 minutes, warmed at reflux for three hours and allowed to cool to room temperature before pouring onto 700 g of ice-water. The resulting mixture is extracted with diethyl ether (4×200 ml).

The combined extracts are washed with saturated aqueous NaHCO₃ (100 ml), water (100 ml) and saturated aqueous NaCl, dried over Na₂SO₄ and concentrated in vacuo to give a brownish yellow solid. The material was used as is in the subsequent reaction. A sample of the residue is recrystallized from ethanol-water to give analytically pure benzyl 3-benzyloxy-5-methoxybenzo[b]thiophene-2-carboxylate as a white crystalline solid: mp 66°–67° C.

Step 2. A solution of the above crude solid in aqueous 1N NaOH (80 ml), methanol (80 ml) and tetrahydrofuran (80 ml) is warmed at reflux for 1.5 hours and allowed to cool to room temperature. The mixture is concentrated in vacuo and taken up in 700 ml of hot, aqueous 1N NaOH and 300 ml of hot methanol, filtered and extracted with hexane (3x). The aqueous solution is treated with 500 g of ice followed by the addition of concentrated HCl until acidic. The resulting precipitate is collected by vacuum filtration and recrystallized from toluene to give 6.5 g (13.7 g theor., 47%) of analytically pure 3-benzyloxy-5-methoxy-benzo[b]thiophene-2-carboxylic acid as a white, crystalline solid: mp=150° C.

Step 3. A solution of 5.6 g (17.2 mmol) of the above carboxylicacid and 3.5 g (21.4 mmol, 1.2 equiv) of 1,1′-carbonyldiimidazole in 110 ml of acetonitrile is warmed at reflux for one hour under nitrogen. The reaction mixture is allowed to cool to room temperature and treated with 1.8 g (21.4 mmol, 1.2 equiv) of anhydrous 5-aminotetrazole and 4.4 g (43.1 mmol, 2.4 equiv) of triethyl amine. The reaction is warmed at reflux for 3.75 hours then poured onto 1000 g of ice-water. The aqueous solution is acidified with aqueous 10% HCl and filtered. The solid is recrystallized from dimethylformamide-water and from 2-methoxyethanol to give 2.7 g (6.8 g theor., 40%) of analytically pure carbamoyltetrazole as a pale yellow solid: mp =206°–207° C.

5,6-Dimethoxy-3-(phenylmethoxy)benzo[b]thiophene-2-carboxylic acid

Also prepared from the corresponding 2-carbonyl chloride using the procedures described in Example 1, Step 1 and Step 2 above with recrystallization from isopropanol is 5,6-dimethoxy-3-(phenylmethoxy)benzo[b]thiophene-2-carboxylic acid: mp=188° C. (dec).

EXAMPLE 2

5-Methoxy-3-phenoxy-N-1H-tetrazol-5-yl-benzo[b]-thiophene-2-carboxamide

Step 1. A solution of 12.2 g (130.1 mmol, 3.0 equiv) of phenol in 40 ml of o-dichlorobenzene is carefully added to a mechanically stirred slurry of 5.2 g (129.5 mmol, 3.0 equiv) of 60% NaH oil dispersion in 70 ml of o-dichlorobenzene under nitrogen atmosphere. The reaction is stirred for 30 minutes and treated with a hot solution of 11.4 g (43.7 mmol) of 3-chloro-5-methoxy-benzo[b]thiophene-2-carboxylchloride (prepared by the method described by Sudabeh Pakray ad Raymond N. Castle in *J Heterocyclic Chem.*, 1986, 23, 1571) in 50 ml of o-dichlorobenzene and 50 ml of tetrahydrofuran. The resulting mixture is heated at 130°–155° C. for one hour and then treated with 1.4 g (4.4 mmol, 0.1 equiv) of tris[2-(2-methoxyethoxy)ethyl]amine and warmed at 130°–135° C. for an additional 22 hours. The reaction is allowed to cool to room temperature and poured onto 600 ml of chloroform and 500 ml of cold aqueous 0.5N NaOH and the layers separated. The aqueous layer is extracted with chloroform (3×). The combined organic layers are washed with cold aqueous 1N NaOH, aqueous 3N HCl and saturated aqueous NaCl, dried over Na$_2$SO$_4$; filtered and concentrated in vacuo down to approximately 200 ml. The solid is isolated by vacuum filtration and washed with aqueous 1N NaOH (2×), water (2×) and diethyl ether (2×) and dried to give 8.0 g (16.5 g theor., 48%) of phenyl 5-methoxy-3-phenoxybenzo[b]thiophene-2-carboxylate as a pale yellow solid. The material is sufficiently pure to use in the subsequent reaction. A sample recrystallized from toluene gives analytically pure product as a white crystalline solid: mp=198° C.

Step 2. Following the method described in Step 2 of Example 1, 7.9 g (21.0 mmol) of the above product gives 5.1 g (6.3 g theor., 81%) of analytically pure 5-methoxy-3-phenoxy-benzo[b]thiophene-2-carboxylic acid as a pale yellow, crystalline solid: mp=197° C. (ethyl acetate-hexane).

Step 3. Following the method described in Step 3 of Example 1, 4.0 g (13.3 mmol) of the above product gives 3.8 g (4.9 g theor., 78%) of analytically pure carbamoyltetrazole as a white solid: mp=251°-252° C. (2-methoxyethanol).

5,6-Dimethoxy-3-phenoxy-benzo[b]thiophene-2-carboxylic acid and
6-methoxy-3-phenoxy-benzo-[b]thiophene-2-carboxylic acid.

Also prepared from the corresponding 2-carbonyl chloride using the procedure described in Example 2Step 1 and Step 2 with recrystallization from ethanol are the 5,6-dimethoxy-3-phenoxy-benzo[b]thiophene-2-carboxylic acid: mp=208° C. (dec), sufficiently pure for the next step and 6-methoxy-3-phenoxybenzo[b]thiophene-2-carboxylic acid: mp=219°-220° C. (dec), sufficiently pure for the next step.

EXAMPLE A1

3-Chloro-6-methoxy-benzo[b]thiophene-2-carbonyl chloride

Thionyl chloride (73 mls, 1.0 mole) is added dropwise to a stirred suspension of 4-methoxycinnamic acid (36.8 g, 0.20 mole) in pyridine (1.6 mls, 0.02 mole) and chlorobenze (200 mls) under argon. The mixture is heated to vigorous reflux. After 72 hours the mixture is filtered and stripped of volatiles under reduced pressure. The residue is dissolved in boiling methyl t-butyl ether (650 mls), filtered, concentrated to 500 lls, and cooled to afford the pure product (22 g): mp=120°-121° C. (See Ried et al, *Ann. Chem.* (1980) 1424–7.)

EXAMPLE A2

3,7-Dichloro-6-methoxy-benzo.b]thiophene-2-carbonyl chloride

Chlorine (24 g) is bubbled into a stirred suspension of 3-chloro-6mmethoxy-benzo[b]thiophene-2-carbonyl chloride (9.2 g, 35 mmoles) in chloroform (200 mls) over a period of 30 minutes. After an additional 45 minutes of stirring at room temperature, the mixture is stripped of volatiles under reduced pressure. The residue is recrystallized from tetrahydrofuran (100 mls) to afford the pure product (6.6 g): mp=174°-175° C.

EXAMPLE A3

3-Chloro-5,6-dimethoxy-benzo[b]thiophene-2-carbonyl chloride

Thionyl chloride (18.3 mls, 0.25 mole) is added dropwise to a stirred suspension of 3,4-dimethoxycinnamic acid (10.4 g, 0.05 mole) in pyridine (0.4 ml, 0.005 mole) and chlorobenzene (50 mls) under argon. The mixture is heated under vigorous reflux for 72 hours, then allowed to cool. The suspended solid is filtered off, rinsed with methyl t-butyl ether, and dried. Recrystallization from tetrahydrofuran (135 mls) gives the product (5.7 g): mp=191°-199° C. A small sample was recrystallized from the same solvent to analytical purity: mp=204°-205° C. (See Wright and Brabander, *J. Het. Chem.* (1971) 711–4.)

EXAMPLE A4

3-Chloro-6-(phenylmethoxy)-benzo[b]thiophene-2-carbonyl chloride

Thionyl chloride (10.6 mls, 0.15 mole) is added dropwise to a stirred suspension of 4-benzyloxycinnamic acid (see Doherty, *J. Am. Chem. Soc.* 77 (1955) 4887–4892) (7.3 g, 0.03 mole) in a mixture of N,N-dimethylformamide (2.2 mls, 0.03 mole), pyridine (0.24 mls, 0.003 mole) and chlorobenzene (40 mls) under argon. The mixture is heated to vigorous reflux for 24 hour, then cooled, and filtered. The filtrate is stripped of volatiles under reduced pressure, and the residue is suspended in ether and filtered to afford the product (3.7 g): mp=132°-134° C.

3-Chloro-5-methoxy-6-(phenylmethoxy)benzo[b]thiophene-2-carbonyl chloride

Prepared by the procedure of Example A4 using 3-methoxy-4-benzyloxy cinnamic acid (Pearl and Beyer, *J. Org. Chem.* 16 (1951) 216) (25.0 g, 88 mmoles) with recrystallization of the residue from toluene gave the 3-chloro-5-methoxy-6-(phenylmethoxy)-benzo[b]-thiophene-2-carbonyl chloride (13.7 g): mp=144°-152° C.

EXAMPLE A5

3-Chloro-6-phenoxy-benzo[b]thiophene-2-carbonyl chloride

Prepared by the procedure described for Example A4 using 4-phenoxycinnamic acid (Watanabe et al, *J. Med. Chem.* (1980) 50–59) (3.1 g, 0.013 mole). Recrystallization of the residue from methyl t-butyl ether (0 mls) affords the product (2.4 g): mp=121°-123° C.

EXAMPLE A6

3-Chloro-5-(phenylmethoxy)-benzo[b]thiophene-2-carbonyl chloride

Prepared by the procedure described for Example A4 using 3-benzyloxycinamic acid (see Example A4 above) (4.0 g, 0.016 mole) Recrystallization of the residue from toluene (18 mls) affords the product (1.5 9) mp=139°-142° C.

EXAMPLE A7

3-Chloro-5-phenoxy-benzo[b]thiophene-2-carbonyl chloride.

Prepared by the procedure of Example A4 using 3-phenoxycinnamic acid (see Brittelli, *J. Org. Chem.* 6 (1981) 2514–2520) (4.4 g, 0.018 mole). Recrystallization of the residue from methyl t-butyl ether (50 mls) affords the pure product (2.3 g): mp=117°–119° C.

EXAMPLE B8

6-Methoxy-3-(1-methylethoxy)-benzo[b]thiophene-2-carboxylic acid

Isopropanol (16.8 g, 280 mmoles) is added dropwise to a stirred suspension of sodium hydride (11.2 g of a 60% dispersion in mineral oil, 280 mmoles) in tetrahydrofuran (50 mls) under argon. After 20 minutes a solution of 3-chloro-6-methoxybenzo[b]thiophene-2-carbonyl chloride (24.2 g, 93 mmoles) in warm tetrahydrofuran (180 mls) is added gradually during 5 minutes, and the mixture is heated under reflux. After 16 hours the mixture is cooled and stripped of solvent under reduced pressure. The residue is partitioned between water (600 mls) and ether (300 mls). The layers are separated and the aqueous phase extracted twice with ether (200 mls). The combined ether extracts are washed with saturated brine, dried over MgSO4, and stripped of solvent under reduced pressure to leave the crude ester as syrup which also contains mineral oil. The syrup is stirred in a mixture of methanol (20 mls) and 1N sodium hydroxide (100 mls), and heated under reflux. After 12 hours the mixture is stirred into water (600 mls) and extracted twice with ether (150 mls). The aqueous solution is stirred and acidified with concentrated HCl, and the resulting precipitate is filtered off, rinsed well with water, and dried to afford the product (11.7 g): mp=155°–156° C. (dec).

The following compounds were prepared from the corresponding 2-carbonyl chlorides using the procedure described in Example B8.

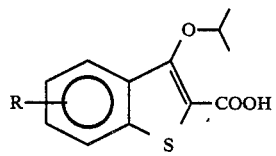

| Example | R (R₁ and/or R₂) | mp °C. |
|---------|------------------|--------|
| B9 | 5,6-DiOMe | 169–170 (dec) |
| B10 | 6-OMe, 7-Cl | 191–192 (dec) |
| B11 | 6-OBn | 163–164 |
| B12* | 6-OPh | 161–162 (dec) |
| B13 | 5-OBn | 160–161 |
| B14 | 5-OPh | 191–192 (dec) |

Me is methyl, Bn is benzyl, Ph is phenyl.
*See following description for procedure.

EXAMPLE B14A 3-(1-Methylethoxy)-5-methoxy-6-(phenylmethoxy)-benzo b]thiophene-2-carboxylic acid Also prepared by the procedure of Example B8 from the corresponding 2-carbonyl chloride with recrystallization from ethanol gave the pure 3-(1-methylethoxy)-5-methoxy-6-(phenylmethoxy)-benzo b]thiophene-2-carboxylic acid mp=183° C. (dec).

*EXAMPLE B12

6-Phenoxy-3(1-methylethoxy)-benzo[b]thiophene-2-carboxylic acid

Isopropanol (1.6 mls, 21 mmoles) is added dropwise to a stirred suspension of sodium hydride (0.85 g of a 60% dispersion in mineral oil, 21 mmoles) in tetrahydrofuran (25 mls) under argon. After 30 minutes, 3-chloro-6-phenoxy-benzo[b]thiophene-2-carbonyl chloride (2.3 g, 7 mmoles) is added, and the mixture is heated under reflux. After 18 hours the mixture is cooled, and stripped of solvent under reduced pressure. Tee residue is partitioned between water (100 mls and ether (60 mls). The layers are separated and the aqueous phase extracted twice with ether (50 mls). The combined extracts are washed with saturated brine, dried over MgSO4, and stripped of solvent under reduced pressure to leave the crude ester as a syrup which also contains mineral oil. The syrup is stirred in a mixture of methanol (5 mls) and 1N sodium hydroxide (10 mls) and heated under reflux. After 24 hours the mixture is poured into water (300 mls), and the precipitate is filtered off, rinsed three times with water then three times with ether, resuspended in water and acidified with concentrated HCl. The precipitate is filtered off, rinsed well with water, and dried: mp=161°–162° C. (dec).

EXAMPLE C15

6M
Methoxy-3-(1-methylethoxy)-N-1H-tetrazol-5-yl-benzo[b]-thiophene-2-carboxamide Carbonyldiimidazole (3.8 g, 23 mmoles) is added to a stirred solution of 6-methoxy-3-(1-methylethoxy)benzo[b]thiophene-2-carboxylic acid (5.4 gg, 20 mmoles) in tetrahydrofuran (75 mls) under nitrogen, and the mixture is heated under reflux. After 75 minutes 5-aminotetrazole (1.66 g. 20 mmoles) is added. After an additional three hours under reflux the mixture is stirred into water (350 mls) and acidified with concentrated HCl. The resulting precipitate is filtered off, rinsed with water, and dried. Recrystallization from DMF/methanol gave the pure product (4.0 g): mp=233°–234? C. (dec).

The following compounds were prepared from the corresponding 2-carboxylic acids using the procedure described in Example C15.

| Example | R (R₁ and/or R₂) | mp °C. |
|---------|------------------|--------|
| C16 | 5,6-DiOMe | 247–248 (dec) |
| C17 | 6-OMe, 7-Cl | 251 (dec) |
| C18 | 6-OBn | 245 (dec) |
| C19 | 6-OPh | 210 (dec) |
| C20 | 5-OBn | 225–226 |

Me, Bn, and Ph are as defined above.

EXAMPLE C20A 3-(1-Methylethoxy)-5-hydroxy-N-H-tetrazol-5yl-benzo[b]-thiophene-2-carboxamide A warm slurry of 3-(1-methylethoxy)-5-(phenylmethoxy)-N-1H-tetrazol-5-yl-benzo[b]thiophene-2carboxamide (1.9 g, 5 mmoles) and 20% palladium on carbon (0.5 g) in acetic acid (250 mls) is shaken under hydrogen (50 psig) in a Parr apparatus. After three hours additional catalyst (0.5 g) is added and the mixture shaken at ambient temperature for 15 hours. The catalyst is removed by filtration and rinsed with warm acetic acid (200 mls). The filtrate is stripped of solvent under reduced pressure and two portions (50 mls) of toluene are added to, then stripped from the residue, leaving the crystalline product. Recrystallization from methanol gave the pure 3-(1-methylethoxy)-5-hydroxy -N-1H-tetrazol-5-yl-benzo[b]thiophene-2-carboxamide (0.7 g): mp=258° C. (dec).

In a manner similar to the procedure of Example C20A the following compound of the formula above, Examples C16-C20, was prepared

| Example | R | mp °C. |
| --- | --- | --- |
| C21 | 5-OPh | 219 (dec) |

Ph is as defined above.

Also prepared from the corresponding 2-carboxylic acid using the procedure described in Example 15 are the compounds of C21A, C21C, and C21D.

EXAMPLE C21A 5,6-Dimethoxy-3-(phenylmethoxy)-N-1H-tetrazol-5-yl-benzo[b]thiophene-2-carboxamide mp=232° C. (dec).

EXAMPLE C21B 3-(1-Methylethoxy)-5-methoxy-6-hydroxy-N-1H-tetrazol-5-Yl-benzo[b]thiophene-2-carboxamide A slurry of 3-(1-methylethoxy)-5-methoxy-6(phenylmethoxy)-N-1H-tetrazol-5-yl-benzo[b]thiophene2-carboxamide imidazole salt (1.55 g, 3 mmoles) and 20% palladium on carbon (0.5 g) in acetic acid (250 mls) is shaken under hydrogen (50 psig) in a Parr apparatus at 40° C. After 19 hours an additional 0.5 g of catalyst and acetic acid (250 mls) are added and shaking continued at 50° C. for 33 hours. The catalyst is filtered from the cooled mixture and rinsed with acetic acid. The filtrate is stripped of solvent under reduced pressure to leave the crystalline product. Recrystallization from methanol gave the pure 3-(1-methylethoxy)-5-methoxy-6-hydroxy-N-1H-tetrazol-5-yl-benzo[b]thiophene-2-carboxamide (0.3 g): mp=245° C. (dec).

EXAMPLE C21C 5,6-Dimethoxy3-phenoxy-N-1H-tetrazol-5-yl-benzo[b]-thiophene-2-carboxamide is prepared according to the procedures of C15 above.

mp=272° C. (dec.)

EXAMPLE C21D

6-Methoxy-3-phenoxy-N-H-tetrazol-5-yl-benzo[b]-thiophene-2-carboxamide is prepared according to the procedure of C15 above.

mp=271°-2° C. (dec).

EXAMPLE B22

6-Methoxy-3-phenylmethoxy)-benzo[b]thiophene-2-carboxylic acid Benzyl alcohol (6.0 mls, 58 mmoles) is added dropwise to a stirred suspension of sodium hydride (2.3 g of a 60% dispersion in mineral oil, 58 mmoles) in tetrahydrofuran (15 mls) under argon. After 20 minutes a solution of 6-methoxy-3-chloro-benzo[b]-thiophene-2-carbonyl chloride (5.0 g, 19 mmoles) in warm tetrahydrofuran (60 ml)) is added during 5 minutes, and the mixture is heated under reflux. After 16 hours the mixture is cooled, and stripped of solvent under reduced pressure. The residue is partitioned between water (300 mls) and ether (150 mls). The layers are separated and the aqueous phase extracted twice with ether (100 mls). The combined ether extracts are washed with saturated brine and dried over MgSO4, then stripped of solvent under reduced pressure to leave the crude ester as a syrup which also contains mineral oil. The syrup is stirred in a mixture of methanol (10 mls) and 1N sodium hydroxide (38 mls) and heated under reflux. After four hours heating is discontinued and the methanol is removed under reduced pressure. The residue is diluted with water (300 mls) and extracted twice with ether (100 mls) The aqueous solution is stirred and acidified with concentrated HCl, and the precipitate is filtered off, rinsed with water, and dried. Recrystallization from ethanol gave the pure product (2.1 g): mp=194° C. (dec).

EXAMPLE C23

6-Methoxy-3-(phenylmethoxy-N-1H-tetrazol-5-yl-benzo[b]thiophene-2-carboxamide.

Prepared by the procedure described for Example C15 using 6-methoxy-3-(phenylmethoyy)-benzo[b]-thiophene-2-carboxylic acid (1.5 g, 5 mmoles). Recrystallization from DMF/MeOH gave the pure product (1.2 g): mp=222° C. (dec)

EXAMPLE C24

3-(1-Methylethoxy)-5-methoxy-6-(phenylmethoxy)-N-1H-tetrazol-5-yl-benzo[b]thiophene-2-carboxamide, imidazole salt Carbonyldiimidazole (0.7 g, 4 mmoles) is added to a stirred solution of 3-(1-methylethoxy)-5-methoxy-6-(phenylmethoxy)-benzo[b]thiophene-2-carboxylic acid (1.6 g, 4 mmole)) in tetrahydrofuran (50 mls) under nitrogen, and the mixture is heated under reflux. After 75 minutes 5-aminotetrazole (0.36 g, 4 mmoles) is added. After an additional three hours under reflux the mixture is stirred into water (500 mls), and the suspended solid is filtered off, rinsed twice with ethanol, twice with ether, and dried to afford the 3-(1-methylethoxy)-5-methoxy-6-(phenylmethoxy)-N-1H-tetrazol-5-yl-benzo[b]thiophene-2-carboxamide, imidazole salt (1.6 g): mp=270° C. (dec).

We claim:

1. A compound of the formula (I)

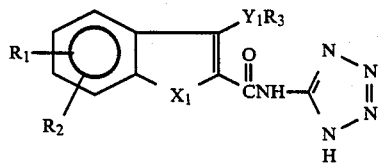

and pharmaceutically acceptable salts thereof; wherein
(1) $X_1$ is oxygen or sulfur;
(2) $R_1$ and $R_2$ are independently hydrogen or $OR_4$ wherein $R_4$ is hydrogen, lower alkyl, aryl, or aralkyl with the proviso that $R_1$ and $R_2$ cannot both be hydrogen at once;
(3) $R_3$ is lower alkyl, aryl, or aralkyl with the proviso that when $R_1$ and $R_2$ are independently hydroxy or alkoxy then $R_3$ cannot be lower alkyl or aralkyl and
(4) $Y_1$ is oxygen.

2. A compound of claim 1 wherein $X_1$ is oxygen.
3. A compound of claim 1 wherein $X_1$ is sulfur.
4. A compound of claim 2 wherein $Y_1$ is oxygen.
5. A compound of claim 3 wherein $Y_1$ is oxygen.
6. A compound of claim 5 wherein $R_3$ is aralkyl which is phenyl or substituted phenyl having one or two substituents selected from halogen, trifluoromethyl, lower alkyl, lower alkoxy, hydroxy, lower alkylthio, $COOR_{10}$ wherein $R_{10}$ is hydrogen or lower alkyl, nitro, amino, or mono- or diloweralkylamino, attached through a lower alkylenyl carbon chain, straight or branched of from one to four carbons.
7. A compound of claim 5 wherein $R_3$ is aryl which is phenyl or substituted phenyl having one or two substituents selected from halogen, trifluoromethyl, lower alkyl, lower alkoxy, hydroxy, lower alkylthio, $COOR_{10}$ wherein $R_{10}$ is hydrogen or lower alkyl, nitro, amino or mono- or diloweralkylamino.
8. A compound of claim 7 which is 5-methoxy-3-phenoxy-N-1H-tetrazol-5-yl-benzo[b]thiophene-2-carboxamide.
9. A compound of claim 5 which is 6-benzyloxy-3-(1-methylethoxy)-N-1H-tetrazol-5-yl-benzo[b]-thiophene-2-carboxamide.
10. A compound of claim 5 which is 6-phenoxy-3-(1-methylethoxy)-N-1H-tetrazol55-yl-benzo[b]-thiophene-2-carboxamide.
11. A compound of claim 5 which is 5-benzyloxy-3(1-methylethoxy)-N-1H-tetrazol-5-yl-benzo[b]-thiophene-2-carboxamide.
12. A compound of claim 5 which is 5-phenoxy-3-(1-methylethoxy)-N-1H-tetrazol-5-yl-benzo[b]-thiophene-2-carboxamide.
13. A compound of claim 7 which is 5,6-dimethoxy-3-phenoxy-N-1H-tetrazol-5-yl-benzo[b]thiophene-2-carboxamide.
14. A compound of claim 7 which is 6-methoxy-3-phenoxy-N-1H-tetrazol-5-yl-benzo[b]thiophene-2-carboxamide.
15. A pharmaceutical composition for treating allergy comprising an antiallergy effective amount of the compound of claim 1 with a pharmaceutically acceptable carrier.
16. A method of treating allergy in a human suffering therefrom which comprises administering a compound of the Formula I of claim 1 in unit dosage form.

* * * * *